US00PP36738P2

(12) United States Plant Patent
Horvath

(10) Patent No.: US PP36,738 P2
(45) Date of Patent: Jun. 10, 2025

(54) ***SCHIZACHYRIUM* GRASS NAMED 'Little Red Fox'**

(50) Latin Name: *Schizachyrium scoparium*
Varietal Denomination: Little Red Fox

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 18/445,889

(22) Filed: Mar. 7, 2024

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

*Primary Examiner* — Susan McCormick Ewoldt
*Assistant Examiner* — Zachariah Allan Kay

(57) ABSTRACT

A new, distinct *Schizachyrium scoparium* grass as illustrated and described, characterized by a height of 69 cm, blue-green colored basal foliage with red and purple fall color.

1 Drawing Sheet

Figure 1:
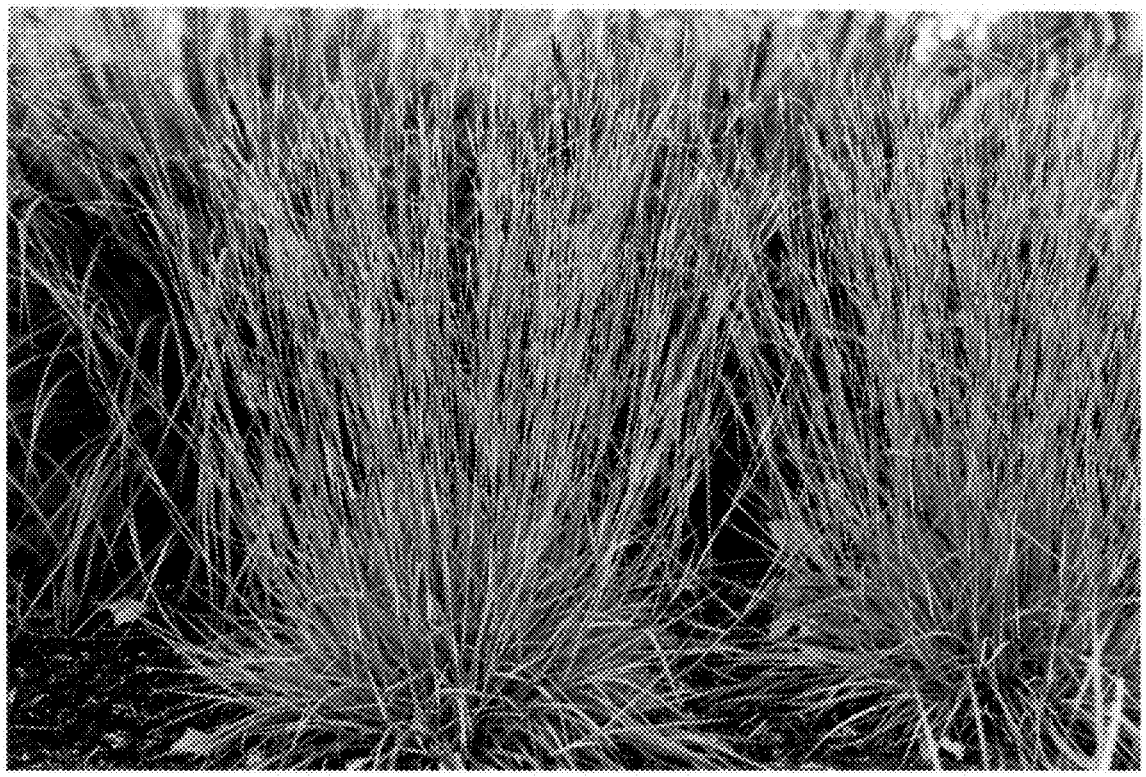

Latin name: *Schizachyrium scoparium.*
Cultivar name: 'Little Red Fox'.

BACKGROUND OF THE INVENTION

The present invention relates to a new form of *Schizachyrium scoparium* plant named 'Little Red Fox'. 'Little Red Fox' is a seedling selection of *Schizachyrium scoparium*, characterized by a height of 69 cm, blue-green colored basal foliage with red and purple fall color. The new plant was grown as a seedling of an unnamed selection of *Schizachyrium scoparium*, by the inventor at a wholesale perennial nursery in Hebron, IL USA in 2019. The selection of this plant was due to its height of 69 cm, and blue-green basal colored foliage with red and purple fall color. Asexual, vegetative division propagation has been the only means of reproduction. Initial vegetative propagation has taken place at Hebron, IL since 2020. In 2022 we planted 500 plants. To date these plants have remained uniform in height, and foliage color. The new *Schizachyrium scoparium* has shown to be stable and identical in reproduction to the parent after making over 1500 vegetative divisions from 2020 to 2023. No plants of *Schizachyrium scoparium* plant named 'Little Red Fox' have been sold in this country, or anywhere in the world, prior to the filing of this application, nor has any disclosure of the new plant been made prior to the filing of this application with the exception of that which was disclosed by the inventor and his nursery in Hebron, IL US and his licensees within one year of the filing of this application and was either derived directly or indirectly from the inventor. Actual first date of sale was Apr. 18, 2023.

SUMMARY OF THE INVENTION

In the following description, color references are made to The Royal Horticultural Society Colour Chart (copyright 2001). The new *Schizachyrium scoparium* plant named 'Little Red Fox' has shown the characteristics of a height of 69 cm, blue-green colored basal foliage with red and purple fall color to be unique and stable. For purpose of the comparison the new plant will be referred to as 'Little Red Fox'.

Plants of 'Little Red Fox' can be compared to plants of *Schizachyrium scoparium* 'Jazz', not patented. 1. 'Little Red Fox' has strong basal blue-green foliage and a height of 69 cm compared to the height of *Schizachyrium scoparium* 'Jazz' which has an average height of 75 cm. 2. 'Little Red Fox' has a foliage color of RHS 137 B with 192 D in the stems coloring to 60 A and N186 D compared to *Schizachyrium scoparium* 'Jazz' which has foliage color close to 189 C.

Plants of 'Little Red Fox' can also be compared to plants of *Schizachyrium scoparium* 'Smoke Signal', U.S. plant Pat. No. 27,433. 1. The 'Little Red Fox' has a height of 69 cm compared to the height of *Schizachyrium scoparium* 'Smoke Signal' which has an average height of 90-120 cm. 2. 'Little Red Fox' has a foliage color of RHS 137 B with 192 D in the stems coloring to 60 A and N186 D compared to *Schizachyrium scoparium* 'Smoke Signal' which has foliage color that is, RHS 138 A and RHS 138 B coloring to N187 A and eventually close to 186 B.

Plants of 'Little Red Fox' can be also be compared to plants of *Schizachyrium scoparium* 'Prairie Blues', not patented. 1. 'Little Red Fox' has a height of 69 cm compared to the height of *Schizachyrium scoparium* 'Prairie Blues' which has an average height of 80-90 cm. 2. 'Little Red Fox' has a foliage color of RHS 137 B with 192 D in the stems coloring to 60 A and N186 D compared to *Schizachyrium scoparium* 'Prairie Blues', which has foliage color close to 190 B.

DESCRIPTION OF PHOTOGRAPHS

FIG. 1. Shows a 2 year old plant in August with red stems in Glencoe, IL USA.

Figure 2:
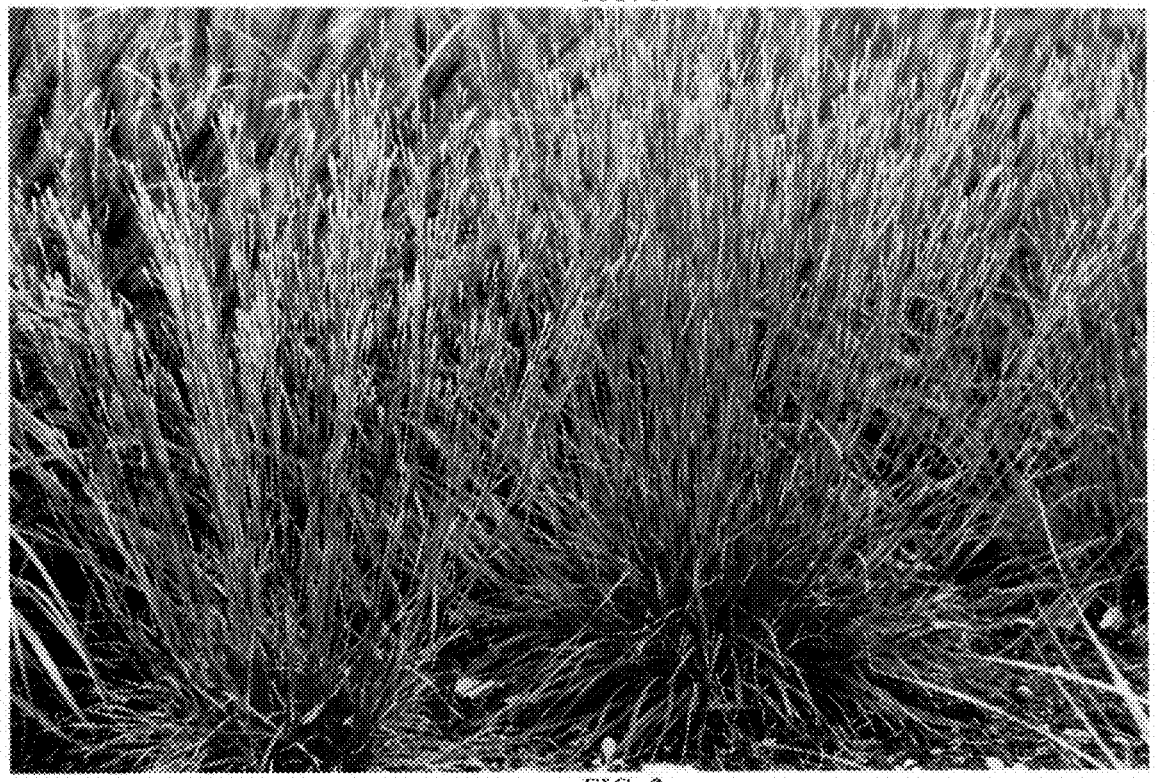

FIG. 2. Shows a 2 year old plant in October with fall foliage color in Glencoe, IL USA.

DETAILED BOTANICAL DESCRIPTION

In the following description, color references are made to The Royal Horticultural Society Colour Chart 2001. The plant herein described is an established 2 year old plant growing in a garden, grown in full sun and irrigated in Hebron, IL USA. Measurements and numerical values represent averages of typical plants.

Botanical classification: *Schizachyrium scoparium* plant named 'Little Red Fox'.

Parentage:

*Female*.—An open pollinated *Schizachyrium scoparium* selection.

*Male*.—An unnamed and unknown *Schizachyrium scoparium* selection.

Propagation: Vegetative division.

Plant description: Overall habit of the new *Schizachyrium scoparium* is clumping with upright culms topped by silvered colored flowers beginning in September. Vigor is moderate.

*Plant height*.—69 cm.

*Plant width*.—60 cm.

Foliage and stems:

*Foliage description*.—Glabrous, flat blade, sheathed from node of attachment to ligule, linear.

*Type*.—Deciduous, grass growing in culms.

*Shape*.—Linear.

*Sheath*.—1 cm wide, 7 cm long, surface — glabrous.

*Ligules*.—Less than 1 mm long and less than 1 mm wide.

*Number of blades*.—Typically 6 blades per stem.

*Blade length*.—10 mm wide, up to 46 cm long, average 35 cm without the sheath.

*Adaxial leaf description*.—Leaf color emerging and summer color is 137 B coloring up to 60 A and N186 D.

*Abaxial leaf description*.—Leaf color emerging and summer color is 137 B coloring up to 60 A and N186 D.

*Veins*.—Parallel, same color as surrounding leaf on both top and bottom of leaf.

*Culm description*.—Erect, cylindrical, typically with 3 leaves.

*Culm or stem diameter*.—1-2 mm average, but typically 1 mm between the nodes and swelling to 2 mm at the base of the internodes.

*Number of culms or stems per clump*.—Over 30.

*Culm color ranges from* 192 D in summer to 60 A and N186 D in fall.

*Node description*.—Cylindrical.

*Number of nodes per culm*.—Average 6.

*Length of internodes*.—Ranges from 3-4 cm.

Flower inflorescence:

*Inflorescence type*.—Terminal raceme with sessile and pedicillate spikelets.

*Rachis*.—1 mm wide and up to 42 cm long, color starts 137 B with 192 D between the nodes in summer coloring to 60 A and N186 D in Fall.

*Overall raceme size*.—1 cm wide, 9-14 cm long.

*Rachilla*.—Less than 1 mm wide, 7 mm long, color starts 137 B with 192 D between the nodes in summer coloring to 60 A and N186 D in Fall.

*Inflorescence color*.—As a whole the color is close to 202 D.

*Spikelet*.—Sessile and pedicellate — Both 8 mm wide 13 mm long, color is close to 202 D.

*Individual floret size*.—1 mm wide, 7 mm long including awn.

*Lower glume*.—1 mm wide, 8 mm long, color starts 137 B coloring to 187 A with fine hairs less than 1 mm wide and 3 mm long, color near 200 D.

*Upper glume*.—1 mm wide, 8 mm long, color starts 137 B coloring to 187 A with fine hairs less than 1 mm wide and 3 mm long, color near 200 D.

*Lemma*.—Outer and inner — both, less than 1 mm, 9 mm long, color starts 137 B coloring up to 187 A.

*Awn size*.—Is less than 1 mm wide and average 13 mm long.

*Pedicels*.—5 to 6 per, 1 mm wide and 9-14 cm long.

*Flower number*.—Approximately 36 florets per rames, average 100 per spikelet, mature spikelet measuring 8 mm wide, 13 mm long.

*Gynoecium*.—Stigma — 2. Color close to 187 A.

*Androecium*.—Anthers — number 3, color — is 187 A.

*Anther size*.—2-3 mm long by 1 mm wide.

*Fertility*.—Fertile with 3 Anthers and 3 Stamens.

*Blooming habit*.—Terminal raceme on up to 69 cm stems.

*Bloom period and duration*.—Last two weeks of August to the end of September.

*Bloom color*.—187 A.

*Fruit or seeds*.—Color is close to 200 D, size is 1 mm wide, 9 mm long.

*Scent*.—No scent.

*Roots*.—Fibrous, and freely branching.

*Fruit*.—Seed identical to the species.

*Hardiness*.—United States Department of Agriculture Zones 4-9.

*Disease resistance*.—Plants are not susceptible to any major pests or diseases.

I claim:

1. A new, distinct *Schizachyrium scoparium* grass named 'Little Red Fox', substantially as described and illustrated, herein.

* * * * *